(12) United States Patent
Watanabe et al.

(10) Patent No.: US 9,925,540 B2
(45) Date of Patent: Mar. 27, 2018

(54) NUCLEIC ACID ANALYSIS APPARATUS, MICROCHIP FOR NUCLEIC ACID ANALYSIS, AND METHOD FOR MOUNTING MICROCHIP IN NUCLEIC ACID ANALYSIS APPARATUS

(71) Applicant: Sony Corporation, Tokyo (JP)

(72) Inventors: Toshio Watanabe, Kanagawa (JP); Masayoshi Akita, Tokyo (JP); Takanori Anaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 229 days.

(21) Appl. No.: 14/417,703

(22) PCT Filed: May 27, 2013

(86) PCT No.: PCT/JP2013/064647
§ 371 (c)(1),
(2) Date: Jan. 27, 2015

(87) PCT Pub. No.: WO2014/020977
PCT Pub. Date: Feb. 6, 2014

(65) Prior Publication Data
US 2015/0251184 A1 Sep. 10, 2015

(30) Foreign Application Priority Data

Aug. 3, 2012 (JP) .................................. 2012-172986

(51) Int. Cl.
*B01L 7/00* (2006.01)
*C12M 1/34* (2006.01)
(Continued)

(52) U.S. Cl.
CPC .............. *B01L 7/5255* (2013.01); *B01L 7/52* (2013.01); *C12Q 1/6846* (2013.01);
(Continued)

(58) Field of Classification Search
CPC ............. B01L 2200/04; B01L 2200/12; B01L 2200/14; B01L 2300/043;
(Continued)

(56) References Cited

U.S. PATENT DOCUMENTS 5,188,963 A   2/1993  Stapleton
5,748,827 A * 5/1998  Holl ........................ H01L 21/68
                                                    385/134
(Continued)

FOREIGN PATENT DOCUMENTS

JP      05-501647      4/1993
JP      2003-534546    11/2003
(Continued)

OTHER PUBLICATIONS

International Search Report issued in connection with International Patent Application No. PCT/JP2013/064647, dated Jul. 23, 2013. (4 pages).

*Primary Examiner* — Michael Hobbs
(74) *Attorney, Agent, or Firm* — Chip Law Group

(57) ABSTRACT

There is provided a nucleic acid analysis apparatus including a heating unit configured to apply heat by contacting a microchip, and a chip holding unit configured to change a position between a first holding position that holds the microchip in midair and a second holding position that holds the microchip in contact with the heating unit.

18 Claims, 11 Drawing Sheets

(51) Int. Cl.
*G01N 35/00* (2006.01)
*C12Q 1/68* (2018.01)
*G01N 35/10* (2006.01)
*G01N 21/64* (2006.01)

(52) U.S. Cl.
CPC .... *G01N 35/00029* (2013.01); *B01L 2200/04* (2013.01); *B01L 2200/12* (2013.01); *B01L 2200/14* (2013.01); *B01L 2300/043* (2013.01); *B01L 2300/0609* (2013.01); *B01L 2300/0654* (2013.01); *B01L 2300/0663* (2013.01); *B01L 2300/0816* (2013.01); *B01L 2300/123* (2013.01); *B01L 2300/1805* (2013.01); *B01L 2300/1822* (2013.01); *B01L 2300/1833* (2013.01); *G01N 21/6452* (2013.01); *G01N 2035/00158* (2013.01); *G01N 2035/00306* (2013.01); *G01N 2035/00316* (2013.01); *G01N 2035/00376* (2013.01); *G01N 2035/1034* (2013.01); *Y10T 29/49998* (2015.01)

(58) Field of Classification Search
CPC ..... B01L 2300/0609; B01L 2300/0654; B01L 2300/0663; B01L 2300/0816; B01L 2300/123; B01L 2300/1805; B01L 2300/1822; B01L 2300/1833; B01L 7/52; B01L 7/5255; C12Q 1/6846; G01N 2035/00158; G01N 2035/00306; G01N 2035/00316; G01N 2035/00376; G01N 2035/1034; G01N 21/6452; G01N 35/00029; Y01T 29/49998

See application file for complete search history.

(56) References Cited

U.S. PATENT DOCUMENTS

| | | | |
|---|---|---|---|
| 6,114,122 | A | 9/2000 | Besemer et al. |
| 2008/0002178 | A1* | 1/2008 | Ogawa ................ B01L 3/50273 356/39 |
| 2010/0279392 | A1 | 11/2010 | Kodama et al. |
| 2011/0312036 | A1 | 12/2011 | Kojima et al. |
| 2012/0064516 | A1 | 3/2012 | Kajihara |

FOREIGN PATENT DOCUMENTS

| | | |
|---|---|---|
| JP | 2012-024072 | 2/2012 |
| JP | 2012-060912 | 3/2012 |
| WO | 2005/107938 | 11/2005 |
| WO | 2008/146754 | 12/2008 |

\* cited by examiner

FIG. 9
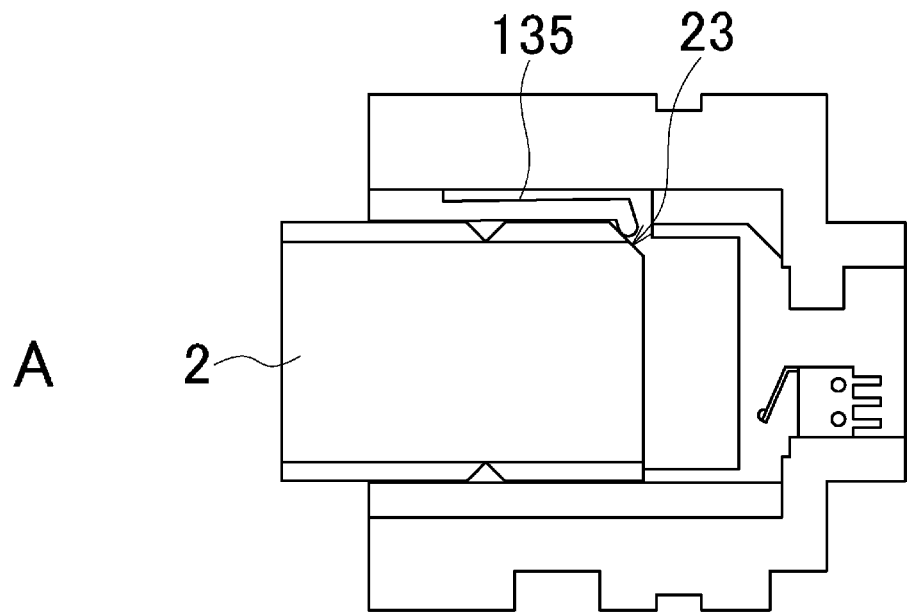
A
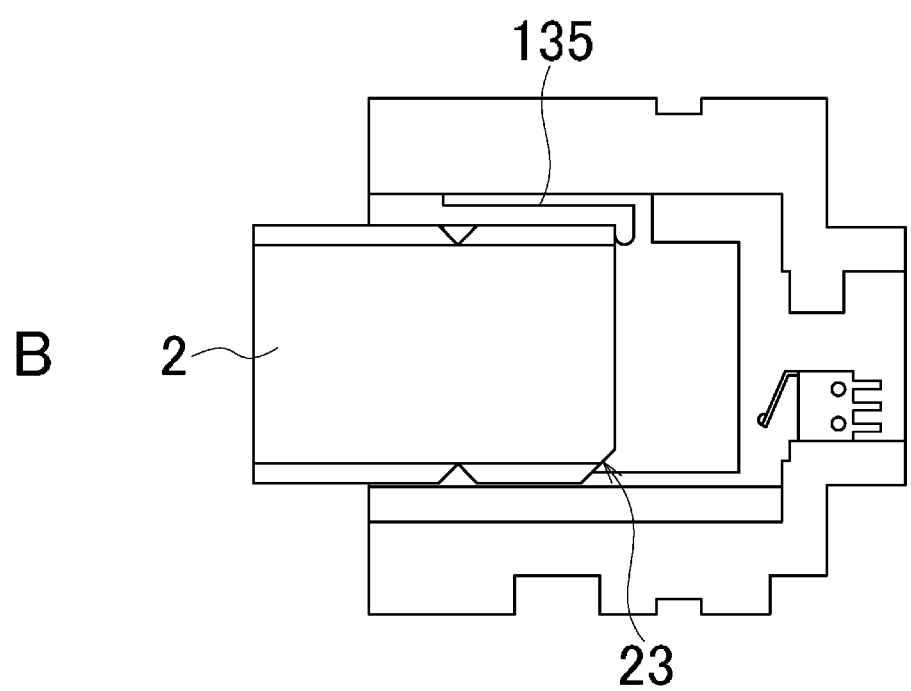
B

NUCLEIC ACID ANALYSIS APPARATUS, MICROCHIP FOR NUCLEIC ACID ANALYSIS, AND METHOD FOR MOUNTING MICROCHIP IN NUCLEIC ACID ANALYSIS APPARATUS

CROSS REFERENCES TO RELATED APPLICATIONS

The present application is a national stage of International Application No. PCT/JP2013/064647 filed on May 27, 2013 and claims priority to Japanese Patent Application No. 2012-172986 filed on Aug. 3, 2012, the disclosure of which is incorporated herein by reference.

BACKGROUND

The present technology relates to a nucleic acid analysis apparatus, a microchip for nucleic acid analysis, and a method for mounting a microchip in that apparatus. More specifically, the present technology relates to a nucleic acid analysis apparatus and the like capable of accurately performing nucleic acid analysis using a microchip.

An apparatus that performs nucleic acid analysis using a substrate (microchip) formed from glass or plastic and in which a reaction area (wells) is arranged has been disclosed. In the nucleic acid analysis apparatus, the microchip is heated with a heater to cause a nucleic acid amplification reaction to occur in the wells, which include a nucleic acid that is to be amplified and a reagent, arranged in the microchip, and the amplified nucleic acid is optically detected.

For example, Patent Literature 1 discloses a nucleic acid analysis apparatus that includes temperature control means for heating a reaction area, irradiation means for irradiating light on the reaction area, and detection means for detecting a scattered light amount of light from the reaction area.

Regarding the present technology, there is a technology called a hot start method for strictly controlling the reaction time of the nucleic acid amplification reaction. The hot start method is a method for providing an intended amplified product in a high yield by avoiding non-specific amplification reactions caused by misannealing of an oligonucleotide primer. In the hot start method, the method is started by heating a mixed solution containing reagents other than enzymes and a nucleic acid to a denaturation temperature of the oligonucleotide primer, and adding enzymes only after reaching the denaturation temperature.

In Patent Literature 2, in order to obtain that same effect as for the hot start method, a "microchip for a nucleic acid isothermal amplification reaction in which at least a part of the substances required for the reaction, which are present in a reaction area acting as the reaction site for an isothermal amplification reaction of a nucleic acid in a state coated with a thin film that melts at a temperature that is a higher than ordinary but lower than the reaction temperature of the reaction". In this microchip for a nucleic acid isothermal amplification reaction, the reaction can be started at an arbitrary timing by heating and melting the thin film coating the substances contained in advance in the reaction area after a sample solution containing the remaining substances and the target nucleic acid has been supplied to the reaction area.

CITATION LIST

Patent Literature

Patent Literature 1: JP 2012-060912A
Patent Literature 2: JP 2012-024072A

SUMMARY

Technical Problem

In a nucleic acid analysis apparatus, in order to obtain stable analysis results with good reproducibility, a heater is pre-heated to a predetermined temperature before analysis is started. By pre-heating the heater, analysis can be started immediately, and the non-specific amplification reactions caused by misannealing of the oligonucleotide primer that can occur until the heater reaches the reaction temperature can be avoided.

On the other hand, when pre-heating the heater, the nucleic acid amplification reaction may start immediately after the microchip has come into contact with the heater. Consequently, the nucleic acid amplification reaction may proceed before the apparatus has started the analysis operation after the operation for mounting the microchip in the apparatus has been completed and the microchip has come into contact with the heater. If such a deviation occurs between the start time of the nucleic acid amplification reaction and the analysis start time, the reaction time cannot be strictly controlled, and accurate analysis results cannot be obtained.

Accordingly, it is an object of the present invention to provide a nucleic acid analysis apparatus capable of controlling the timing of a reaction starting without requiring a complex configuration or control.

Solution to Problem

In order to solve the problem, according to an embodiment of the present disclosure, there is provided a nucleic acid analysis apparatus including a heating unit configured to apply heat by contacting a microchip, and a chip holding unit configured to change a position between a first holding position that holds the microchip in midair and a second holding position that holds the microchip in contact with the heating unit.

The nucleic acid analysis apparatus includes an opening/closing structure configured from a hinge. The chip holding unit is connected by the hinge and moves between the first holding position and the second holding position in coordination with opening and closing of the opening/closing structure. Specifically, the chip holding unit moves to the first holding position in coordination with an opening operation of the opening/closing structure, and moves to the second holding position in coordination with a closing operation of the opening/closing structure.

In this nucleic acid analysis apparatus, by opening the opening/closing structure and then closing the opening/closing structure after the microchip has been held in a chip holding unit that is at a first position, the microchip held in the chip holding unit can be brought into contact with the heating unit for the first time. In other words, with this nucleic acid analysis apparatus, the microchip mounted in the chip holding unit during opening of the opening/closing structure can be prevented from coming into contact with the heating unit until the opening/closing structure is closed. Therefore, with this nucleic acid analysis apparatus, the timing of the start of the nucleic acid reaction can be precisely controlled by making the closing operation of the opening/closing structure and the start of heating the microchip match.

According to an embodiment of the present disclosure, it is preferable for the nucleic acid analysis apparatus to have an insertion opening of the microchip in the chip holding unit. A shape of the insertion opening is a perpendicular cross-section shape of the microchip in an insertion direction, preferably. The chip holding unit includes a flexible member having a hook-shaped tip portion extending in the insertion direction of the microchip, preferably. In a state in which the microchip is inserted in the chip holding unit, the tip portion of the flexible member fits into a groove formed on a side peripheral portion of the microchip. In addition, in a state in which the microchip is inserted in the chip holding unit, the tip portion of the flexible member abuts only one face of the groove formed in a V shape, and urges the microchip in the insertion direction, preferably.

According to an embodiment of the present disclosure, the nucleic acid analysis apparatus includes an upper unit and a lower unit that are each connected by the hinge in a manner that enables them to be opened and closed, and each include the heating unit. The lower unit includes a light source, a lens, an optical filter, and a lower heater, and the upper unit includes an upper heater, a detection filter, a lens, and a detector. The light source is an LED array, and the detector is a PDIC array.

It is preferable for the nucleic acid analysis apparatus to include a sensor configured to detect opening and closing of the upper unit and the lower unit. In addition, a sensor configured to detect the inserted microchip is provided in the chip holding unit, preferably.

In addition, According to an embodiment of the present disclosure, there is also provided a method for mounting a microchip in a nucleic acid analysis apparatus, the method including a step of moving a chip holding unit connected by a hinge to a first holding position for holding the microchip in midair, in coordination with an opening operation of an opening/closing structure by the hinge, a step of mounting the microchip in the chip holding unit moved to the first holding position, and a step of moving the chip holding unit in which the microchip is mounted to a second holding position for holding the microchip in contact with a heating unit, in coordination with a closing operation of the opening/closing structure.

In the present technology, the term "nucleic acid amplification reaction" includes a PCR (polymerase chain reaction) method that involves a temperature cycle, and a variety of isothermal amplification methods that do not involve a temperature cycle. Examples of the isothermal amplification methods include a LAMP (Loop-Mediated Isothermal Amplification) method, an SMAP (SMart Amplification Process) method, a NASBA (Nucleic Acid Sequence-Based Amplification) method, an ICAN (Isothermal and Chimeric primer-initiated Amplification of Nucleic acids) method (registered trademark), a TRC (transcription-reverse transcription concerted) method, a SDA (strand displacement amplification) method, a TMA (transcription-mediated amplification) method, a RCA (rolling circle amplification) method and the like. In addition, the term "nucleic acid amplification reaction" widely includes nucleic acid amplification reactions for amplifying nucleic acids at a varying temperatures or at a constant temperature. Further, the term "nucleic acid amplification reaction" also includes reactions involving quantification of amplified nucleic acid strands such as a real time PCR (RT-PCR) method and an RT-RAMP method.

Advantageous Effects of Invention

According to the present technology, provided is a nucleic acid analysis apparatus capable of precisely controlling the timing of a reaction starting without requiring a complex configuration or control.

Additional features and advantages are described herein, and will be apparent from the following Detailed Description and the figures.

BRIEF DESCRIPTION OF THE FIGURES

FIG. 9 is a diagram illustrating a misinsertion prevention function of the lever 135.

FIG. 11 is a flowchart illustrating operation of the nucleic acid analysis apparatus 1a.

DETAILED DESCRIPTION

Figure 1:
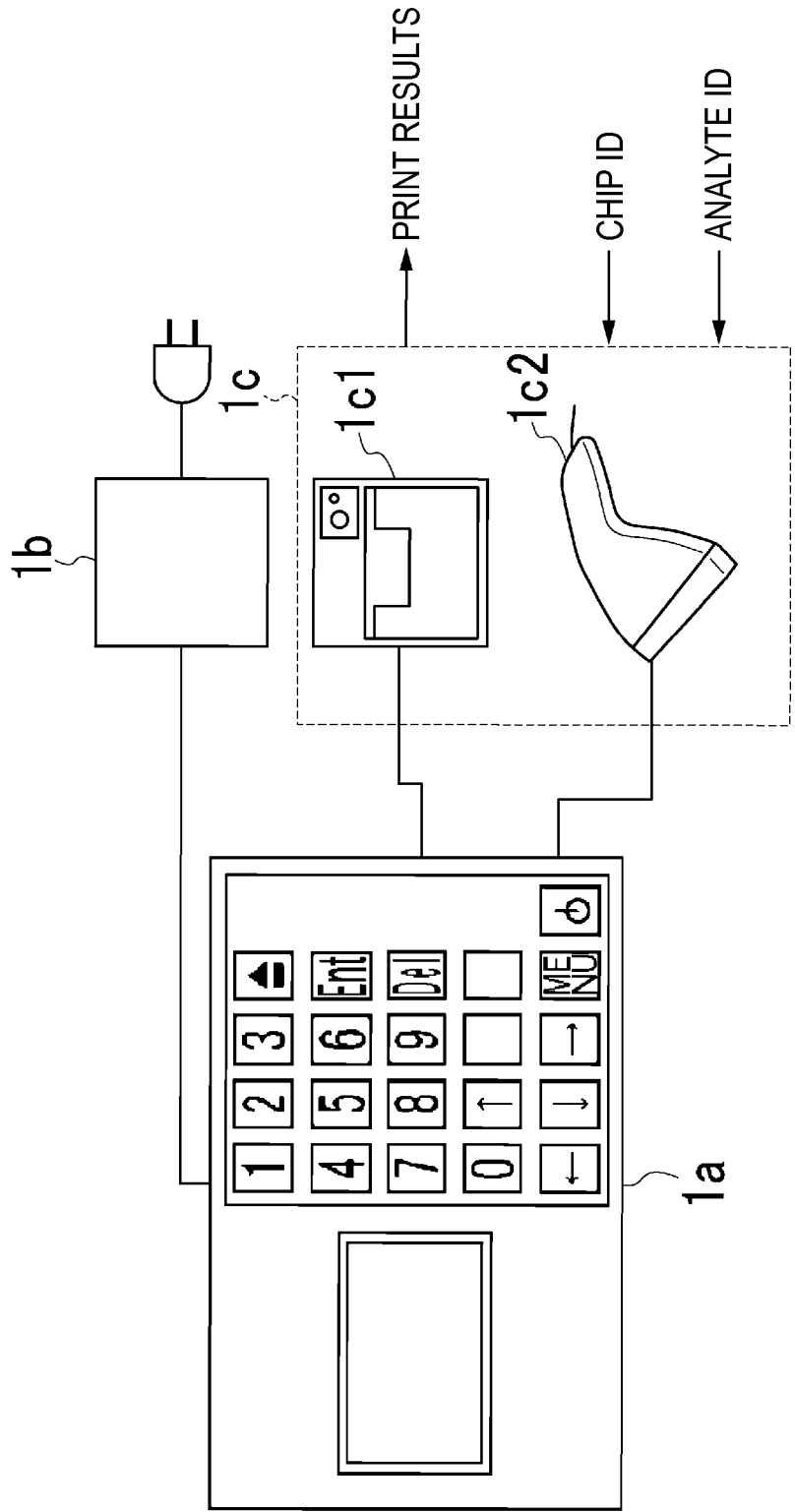
FIG. 1 is a diagram illustrating a configuration of a nucleic acid analysis apparatus 1a according to the present technology.

Hereinafter, preferred embodiments of the present invention will be described in detail with reference to the appended drawings. Note that, in this specification and the drawings, elements that have substantially the same function and structure are denoted with the same reference signs, and repeated explanation is omitted. The description will be made in the following order.
1. Nucleic acid analysis apparatus
(1) Nucleic acid analysis apparatus
(2) Upper unit and lower unit
(3) Chip holder
(3-1) Flip-up mechanism
(3-2) Misinsertion prevention mechanism
(4) Microchip
2. Nucleic acid analysis apparatus operation
3. Analysis apparatus
1. Nucleic Acid Analysis Apparatus
(1) Nucleic Acid Analysis Apparatus FIGS. 1 to 3 are diagrams illustrating a configuration of a nucleic acid analysis apparatus according to the present technology.

A nucleic acid analysis apparatus 1a according to the present technology includes an AC adapter 1b and an input/output interface 1c (refer to FIG. 1). A compact display capable of displaying simple information and keys capable of simple inputs are arranged on an upper face of the body of the nucleic acid analysis apparatus 1a. An LCD display may be used for the compact display. Further, as the keys, a keypad (numeric keys), and a below-described power button and eject button are provided. The input/output interface 1c includes, for example, a printer 1c1 for outputting nucleic acid analysis results, and a code reader 1c2 for reading an identifier attached to a microchip for nucleic acid analysis (hereinafter also simply referred to as "microchip") that is mounted in the apparatus. The input/output interface 1c may also include a display, a keyboard and the like that are used to output analysis results and input an identifier, for example.

Examples of the identifier attached to the microchip include an item in which a chip ID indicating a production number of the microchip and the type of reagents contained in the wells, an analyte ID indicating the origin of a sample and the like, are readably recorded. For example, a commonly-used barcode may be employed.

Figure 2:
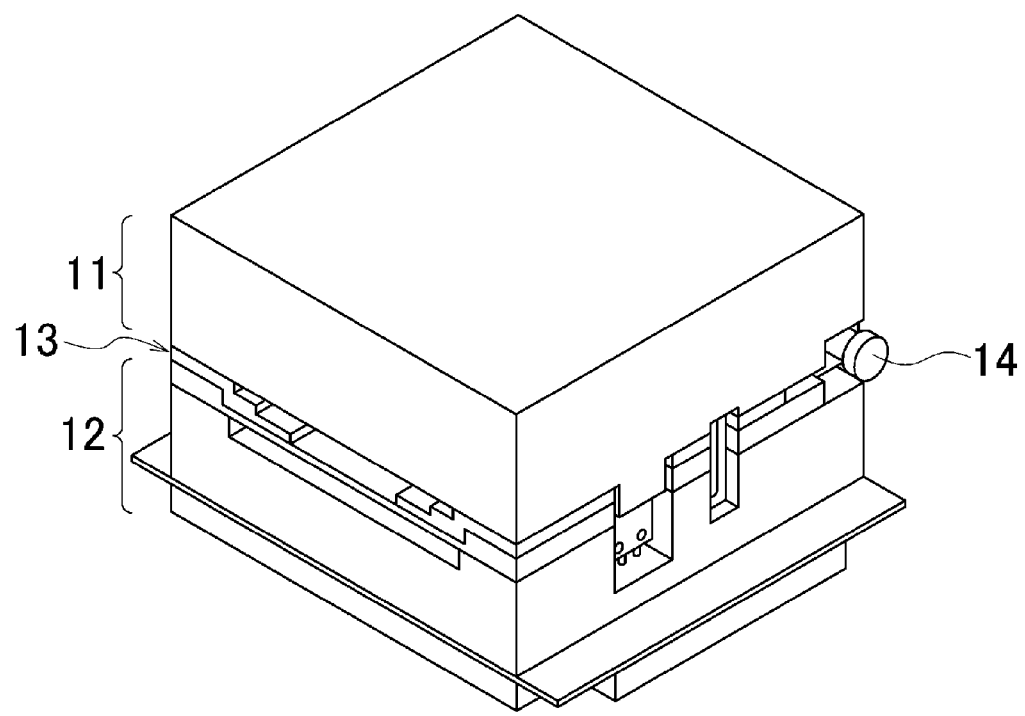
FIG. 2 is a diagram illustrating the nucleic acid analysis apparatus 1a in a state in which an upper unit 11 and a lower unit 12 are closed.
Figure 3:
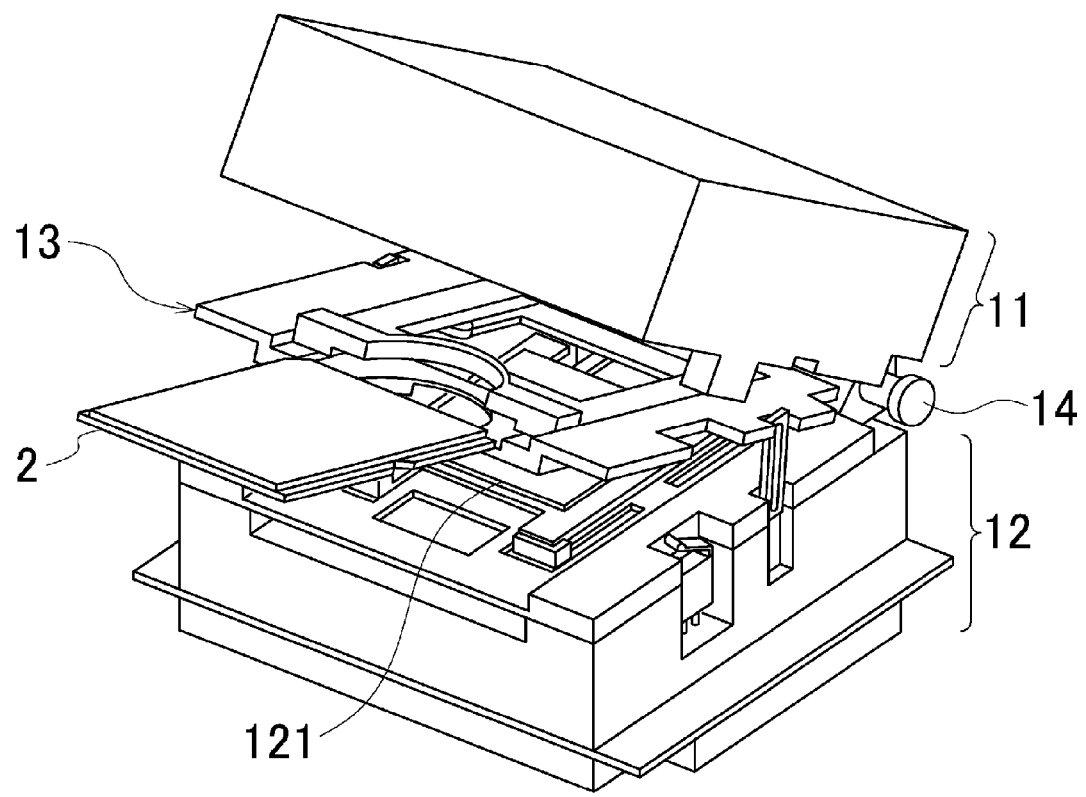
FIG. 3 is a diagram illustrating the nucleic acid analysis apparatus 1a in a state in which the upper unit 11 and the lower unit 12 are open.

The nucleic acid analysis apparatus 1a includes an upper unit 11, a lower unit 12, and a chip holder 13 (refer to FIG. 2). The upper unit 11 and the lower unit 12 are connected in a manner that enables them to be opened and closed. Further, the chip holder 13 is also connected by a hinge 14 to both the upper unit 11 and the lower unit 12. FIG. 2 illustrates the nucleic acid analysis apparatus 1a in a state in which the upper unit 11 and the lower unit 12 are closed. FIG. 3 illustrates the nucleic acid analysis apparatus 1a in a state in which the upper unit 11 and the lower unit 12 are open. When the upper unit 11 and the lower unit 12 are in an open state, the chip holder 13 is positioned between the upper unit 11 and the lower unit 12. The microchip 2 is mounted in the apparatus by inserting the microchip 2 into the chip holder 13 in a state in which the upper unit 11 and the lower unit 12 are open.

(2) Upper Unit and Lower Unit

Figure 4:
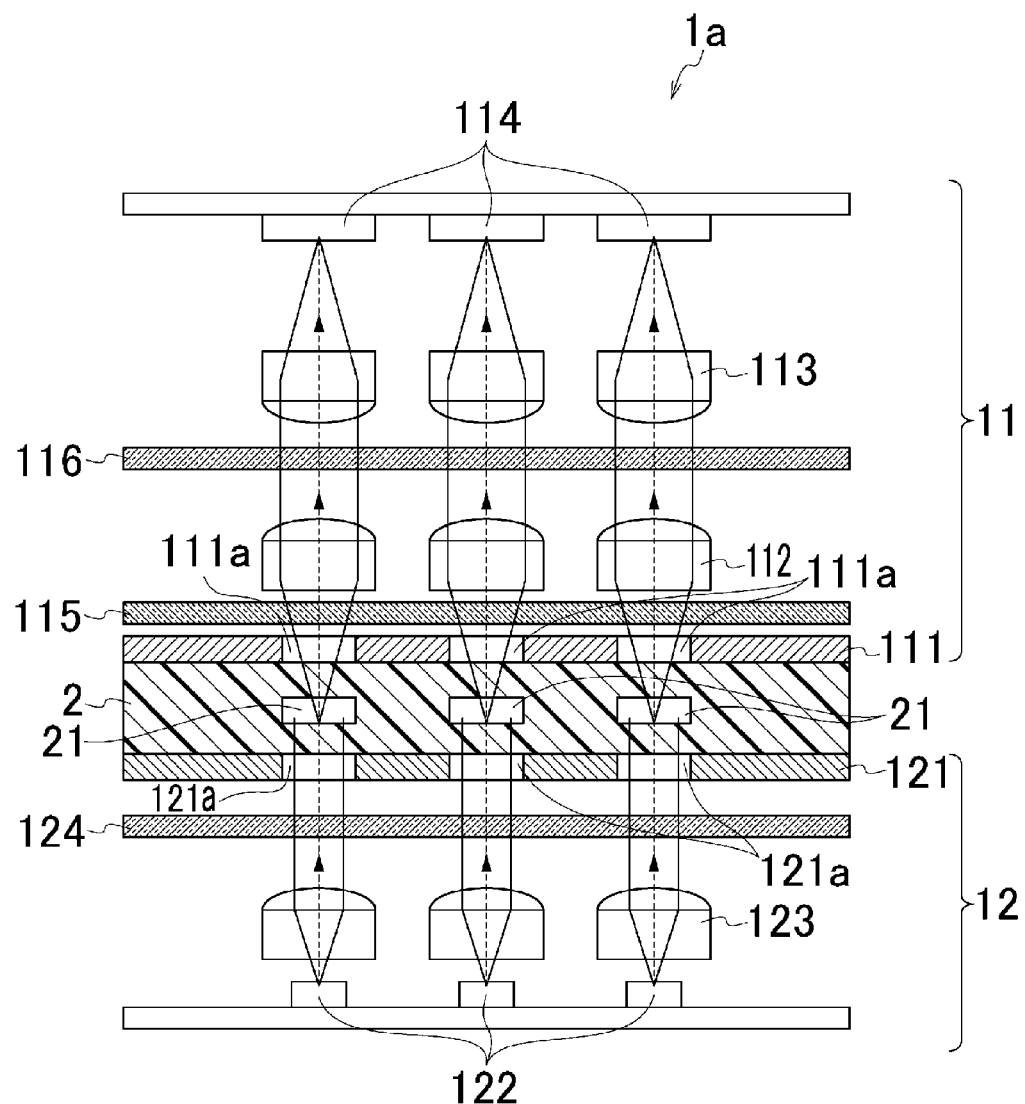
FIG. 4 is a diagram illustrating a configuration of the upper unit 11 and the lower unit 12.

A configuration of the upper unit 11 and the lower unit 12 will be described with reference to FIG. 4. The upper unit 11 and the lower unit 12 include a structure for optically detecting a nucleic acid amplification reaction in a reaction area (hereinafter referred to as "wells 21") of the microchip 2.

Examples of the detection method of the nucleic acid amplification reaction in the nucleic acid analysis apparatus 1a include, but are not especially limited to, a method that uses a fluorescent reagent that produces fluorescence or is extinguished based on the progress of the nucleic acid amplification reaction, and a method that detect changes in light scattering or absorption or changes in polarized light in a reaction solution that occur as the nucleic acid amplification reaction progresses.

First, the configuration of the lower unit 12 will be described in detail. The lower unit 12 includes a lower heater 121, a light source 122, a lens 123, and an optical filter 124. It is preferred that a plurality of the light sources 122 and lenses 123 are arranged to correspond to the plurality of wells 21 that are arranged in the microchip 2. Further, it is preferred that an opening 121a for transmitting the light emitted from each light source 122 is provided in the lower heater 121.

The lower heater 121 heats a reaction solution in the wells 21 to the reaction temperature of the nucleic acid amplification reaction by, in a state in which the upper unit 11 and the lower unit 12 are closed, contacting the back face of the microchip 2 mounted in the chip holder 13 to apply heat to the wells 21. It is noted that although illustration of the chip holder 13 is omitted in the diagram, the microchip 2 is held by the chip holder 13 in a state in which the microchip 2 is in contact with the lower heater 121 and the below-described upper heater 111.

For the heater 21, a heat block formed from a metal such as aluminum or gold that is generally used in conventionally-known nucleic acid analysis apparatuses may be employed. Further, the heater 21 may be a ceramic heater, a Peltier heater, an electrically-heated wire and the like. Further, a transparent conductive membrane, such as an ITO heater, that is optically transparent can also be used. It is noted that if the wells 21 are transparent, the opening 121a does not need to be provided.

The light source 122 may be appropriately selected based on the optical detection method. For the light source 122, a laser light source, a white or monochrome light-emitting diode (LED), a mercury lamp, a tungsten lamp and the like can be employed. A combination of two or more of these light sources may be used. Examples of laser light sources that can be used include, but are not especially limited to, light sources that emit light, such as a semiconductor laser, an argon ion (Ar) laser, a helium-neon (He—Ne) laser, a dye laser, and a krypton (Kr) laser. It is preferred that the light source 122 is configured as an LED array having excellent uniformity. By using an LED array, the analysis accuracy is increased by suppressing stray light, power consumption and production costs are suppressed, and the size of the apparatus can be reduced.

The light emitted from the light source 122 is transmitted through the lens 123 and an excitation filter 124, passes through the opening 121a of the lower heater 121, and is irradiated on the wells 21. At this stage, if the lower heater 121 is not optically transparent, the opening 121a functions as an aperture to prevent the irradiation of light emitted from the light source 122 that has crossed over from an adjacent well 21. It is noted that the excitation filter 124 is arranged as necessary for selectively transmitting light having a specific wavelength component among the light emitted from the light source 122.

The upper unit 11 includes an upper heater 111, lenses 112 and 113, a detector 114, and detection filters 115 and 116. It is preferred that a plurality of the lenses 112 and 113, and detectors 114 are arranged to correspond to the plurality of wells 21. Further, it is preferred that an opening 111a for transmitting the light from the wells 21 to the detector 114 is provided in the upper heater 111.

When the upper unit 11 and the lower unit 12 are in a closed state, the upper heater 111 is in contact with a front face of the microchip 2 mounted in the chip holder 13. The upper heater 111, which is similarly configured to the lower heater 121, heats the reaction solution in the wells 21 to the reaction temperature of the nucleic acid amplification reaction by applying heat to the wells 21.

The light produced from the wells 21 due to the irradiation of light from the light source 122 is transmitted through the detection filter 115, the lens 112, the detection filter 116, and the lens 113, hits the detector 114, and is detected. At this stage, if the upper heater 111 is not optically transparent, the opening 111a functions as an aperture to prevent light produced from an adjacent well 21 that crosses over from being detected.

The detected light is, based on the optical detection method of the nucleic acid amplification reaction, transmitted light, scattered light from a reaction product, fluorescence produced from a fluorescent reagent and the like. The detection filters 115 and 116 are arranged as necessary for selectively transmitting light having a specific wavelength component to the detector 114.

For the detector 114, a photo diode (PD) array, an area image sensor such as a CCD image sensor and a CMOS sensor, a PMT (photomultiplier tube) and the like is used. It is preferred that the detector 114 is a PDIC array having little noise. By using a PDIC array, analysis accuracy can be increased, and the number of parts can be reduced.

(3) Chip Holder (3-1) Flip-Up Mechanism

Figure 5:
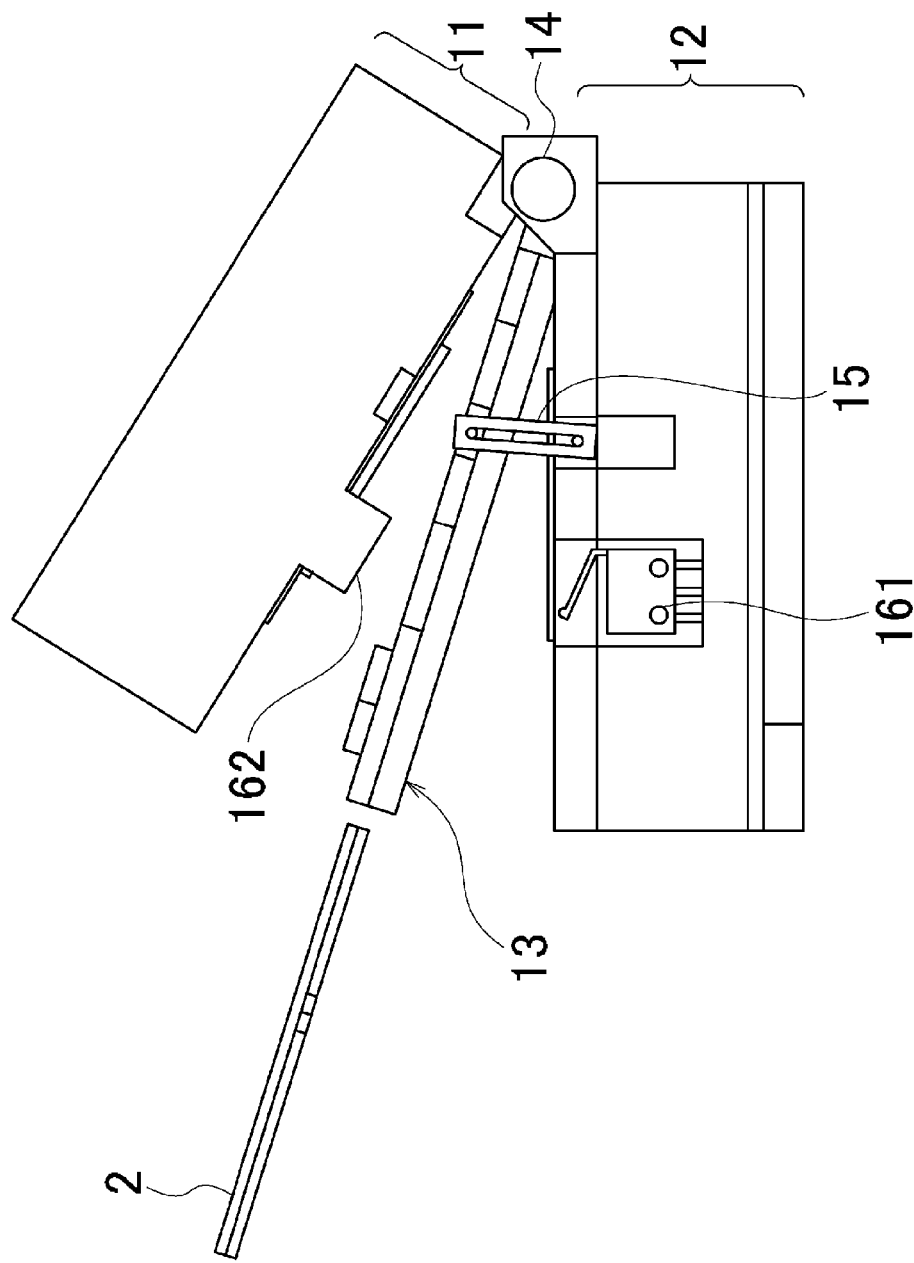
FIG. 5 is a diagram illustrating the nucleic acid analysis apparatus 1a and a microchip 2 in a state in which the upper unit 11 and the lower unit 12 are open.
Figure 6:
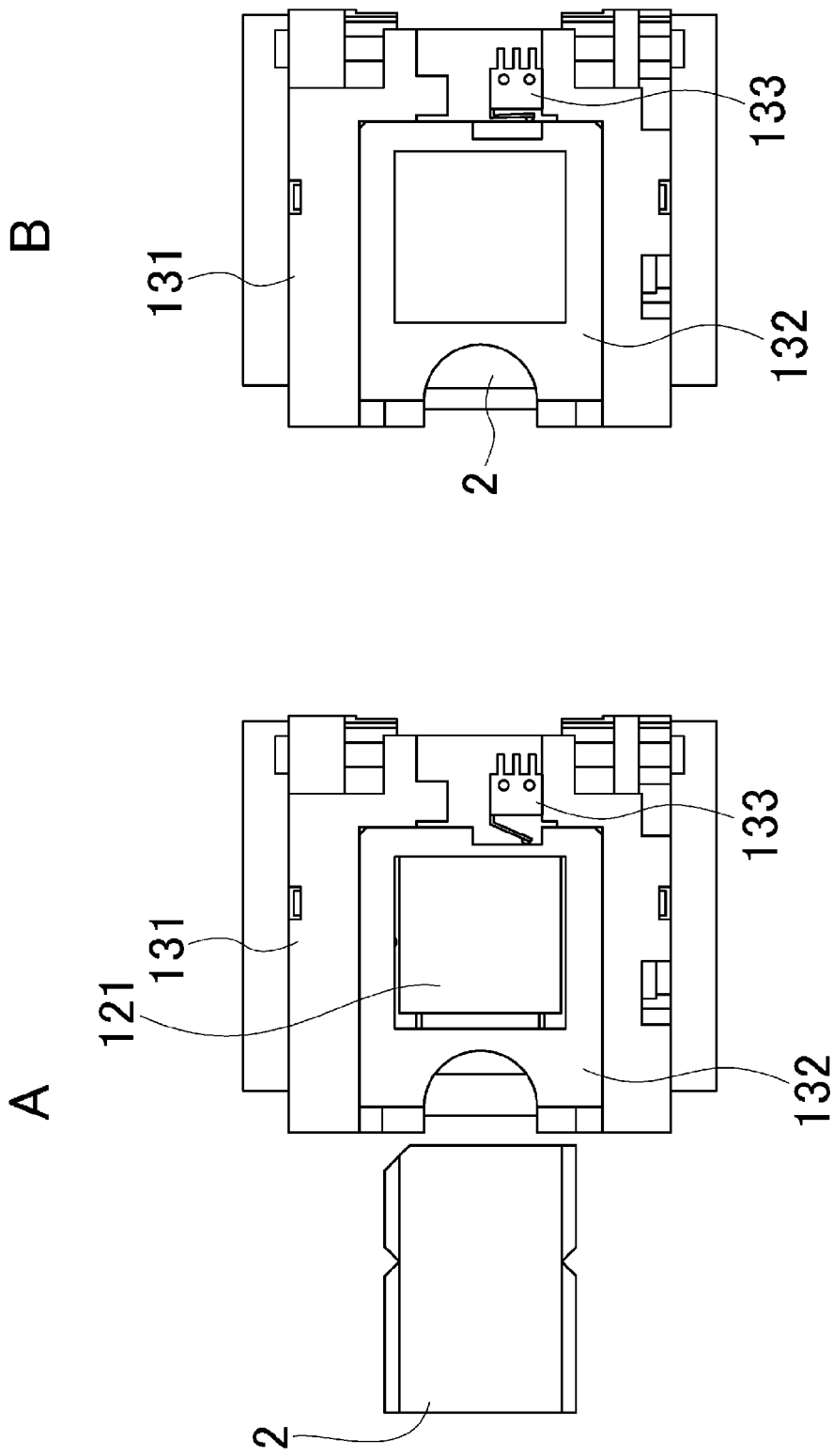
FIG. 6 is a diagram illustrating a configuration of a chip holder 13.

FIG. 5 illustrates the chip holder 13 in a state in which the upper unit 11 and the lower unit 12 are open, and the microchip 2 is inserted into the chip holder 13. In a state in which the upper unit 11 and the lower unit 12 are open, as illustrated the diagram, the chip holder 13 is positioned away from both the upper unit 11 and the lower unit 12.

The chip holder 13 is urged in the opening direction of the upper unit 11 about the hinge 14 by an elastic member such as a helical torsion coil spring. Consequently, in coordination with the opening action of the upper unit 11, the chip holder 13 is lifted and flipped up in the same direction by the elastic member. It is noted that the upper unit 11 is also urged in the opening direction about the hinge 14 by an elastic member.

It is preferred that the opening angle of the chip holder 13 when the upper unit 11 and the lower unit 12 are in an open state (the angle formed by the lower unit 12 with the chip holder 13) is about half the opening angle of the upper unit 11 (the angle formed by the lower unit 12 with the chip holder 11). This is to facilitate the insertion operation of the microchip 2 into the chip holder 13. However, the opening angle of the chip holder 13 is not especially limited, as long as the chip holder 13 does not come into contact with the upper unit 11 or the lower unit 12.

A mechanism for controlling the opening angle of the chip holder 13 to an angle like that described above is provided in the nucleic acid analysis apparatus 1*a*. Specifically, as illustrated in the diagram, a braking member 15 that is in contact with the lower unit 12 and the chip holder 3 is provided. A groove that a pin provided on each of the lower unit 12 and the chip holder 13 fits into is provided in the braking member 15. The pin on the chip holder 13 side is slidably received by this groove. The braking member 15 controls the opening angle of the chip holder 13 to a predetermined angle by restricting the slide amount of the pin on the chip holder 13 side.

The following configurations can also be employed as the configuration for flipping up the chip holder 13 to a predetermined opening angle in coordination with the opening operation of the upper unit 11. For example, the chip holder 13 can also be flipped up by, when opening the upper unit 11, bringing the edge of the upper unit 11 that connects to the hinge 14 into contact with the edge of the chip holder 13 that connects to the hinge 14 to apply a force for opening the chip holder 13. In this case, the above-described force starts to act when the edge of the upper unit 11 that connects to the hinge 14 and the edge of the chip holder 13 that connects to the hinge 14 come into contact after the opening angle of the upper unit 11 has reached a predetermined angle (e.g., half the maximum opening angle).

Further, for example, a gear that is rotated by the opening operation of the upper unit 11 can be provided near the hinge 14, and the chip holder 13 flipped up by the power of a gear that engages and rotates with this gear. In this case, by appropriately setting the number of teeth of the two gears, the opening angle of the chip holder 13 can be controlled to a desired angle.

In the nucleic acid analysis apparatus 1*a*, based on the respective above-described configurations, the chip holder 13 is flipped up to a predetermined opening angle in coordination with the opening operation of the upper unit 11. At this flipped-up position (a first holding position), the chip holder 13 is separated from the upper unit 11 and the lower unit 12. Consequently, the microchip 2 inserted into the chip holder 13 is held in midair without contacting the upper heater 111 arranged in the upper unit 11 and the lower heater 121 arranged in the lower unit 12.

After the microchip 2 has been inserted into the chip holder 13, the chip holder 13 is restrained by the upper unit 11 so that when the upper unit 11 and the lower unit 12 are closed, the chip holder 13 is sandwiched between the upper unit 11 and the lower unit 12 (refer to FIG. 2). Consequently, the chip holder 13 moves to a position in which the microchip 2 is held in contact with the upper heater 111 and the lower heater 121 (a second holding position).

An opening/closing detection sensor 161 illustrated in FIG. 5 detects the opening and closing of the upper unit 11 and the lower unit 12. When the upper unit 11 and the lower unit 12 are closed, a protrusion 162 provided on the upper unit 11 contacts the opening/closing detection sensor 161, and a close operation is detected.

(3-2) Misinsertion Prevention Mechanism

The configuration of the chip holder 13 will now be described in more detail with reference to FIGS. 6 to 10. The chip holder 13, which is formed from a holder outer frame 131 and a holder inner frame 132, includes a chip detection sensor 133 for detecting the microchip 2 inserted from an insertion opening 134.

Figure 7:
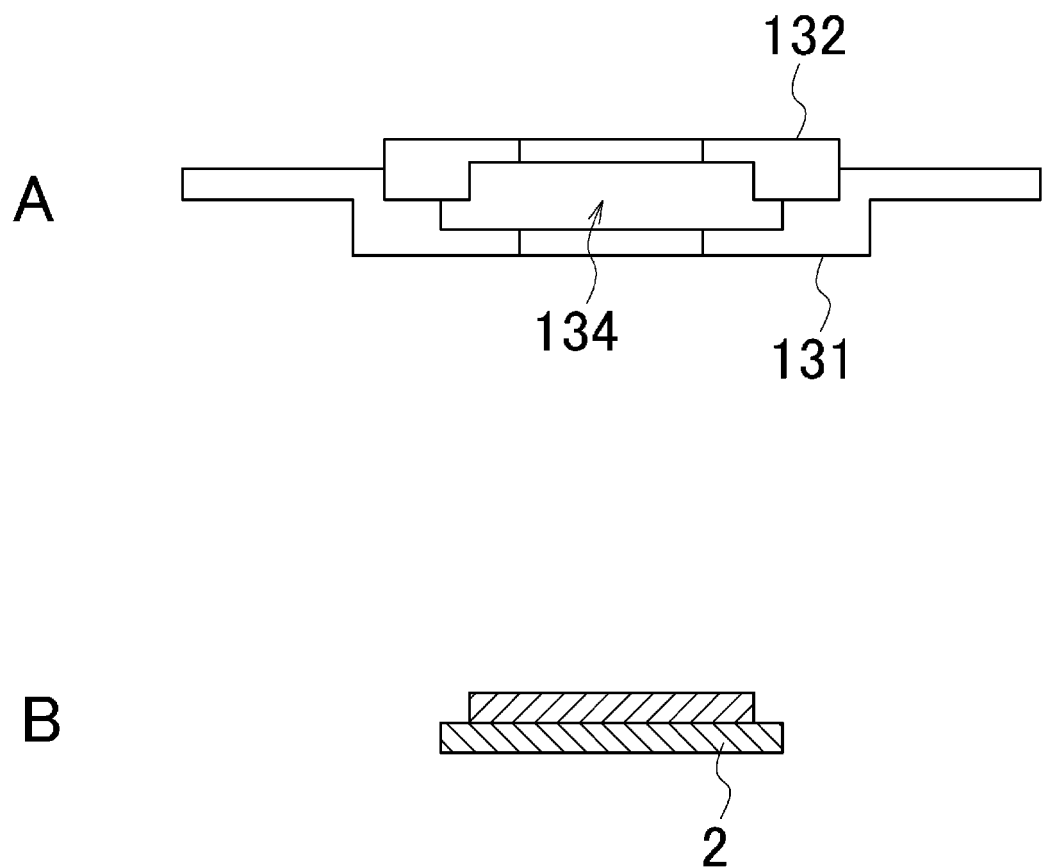
FIG. 7 is a diagram illustrating a configuration of an insertion opening 134 of the chip holder 13.

The insertion opening 134 is formed in a shape that matches a perpendicular cross-section in the insertion direction of the microchip 2 so that the back and front of the microchip 2 are not mistakenly inserted. FIG. 7 illustrates a specific example of the shape of the insertion opening 134 (7A) and the cross-sectional shape of the microchip 2 (7B). In this example, the cross-sectional shape of the microchip 2 is different on the front face side and the back face side (length in the traverse direction in the diagram), and the insertion opening 134 is made to match this cross-sectional shape. The microchip 2 having such a cross-sectional shape can be produced by laminating two substrate layers having different sizes. It is noted that the cross-sectional shape of the insertion opening 134 and the microchip 2 is not limited to the example illustrated here.

Figure 8:
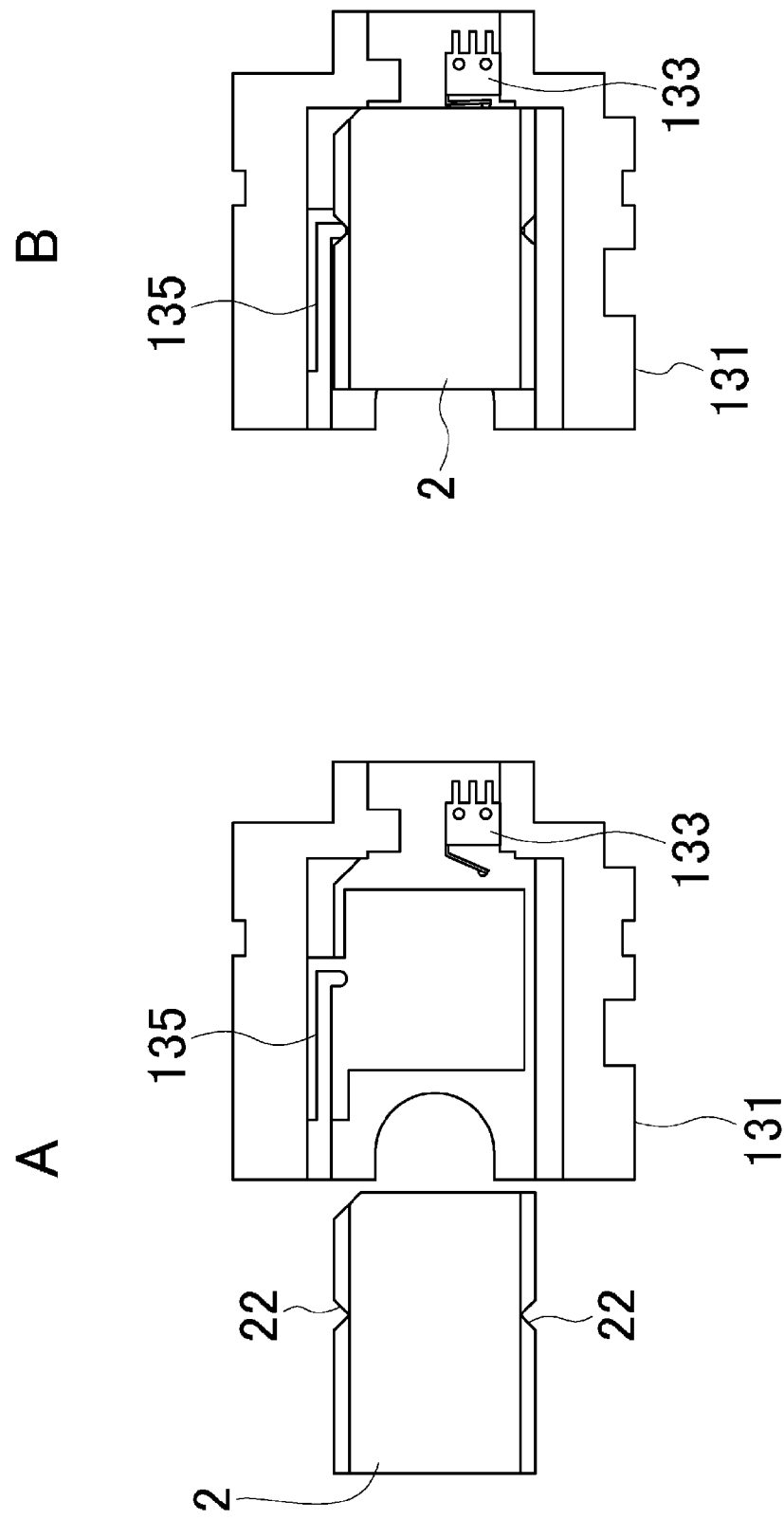
FIG. 8 is a diagram illustrating a configuration of a lever 135 of the chip holder 13.
Figure 10:
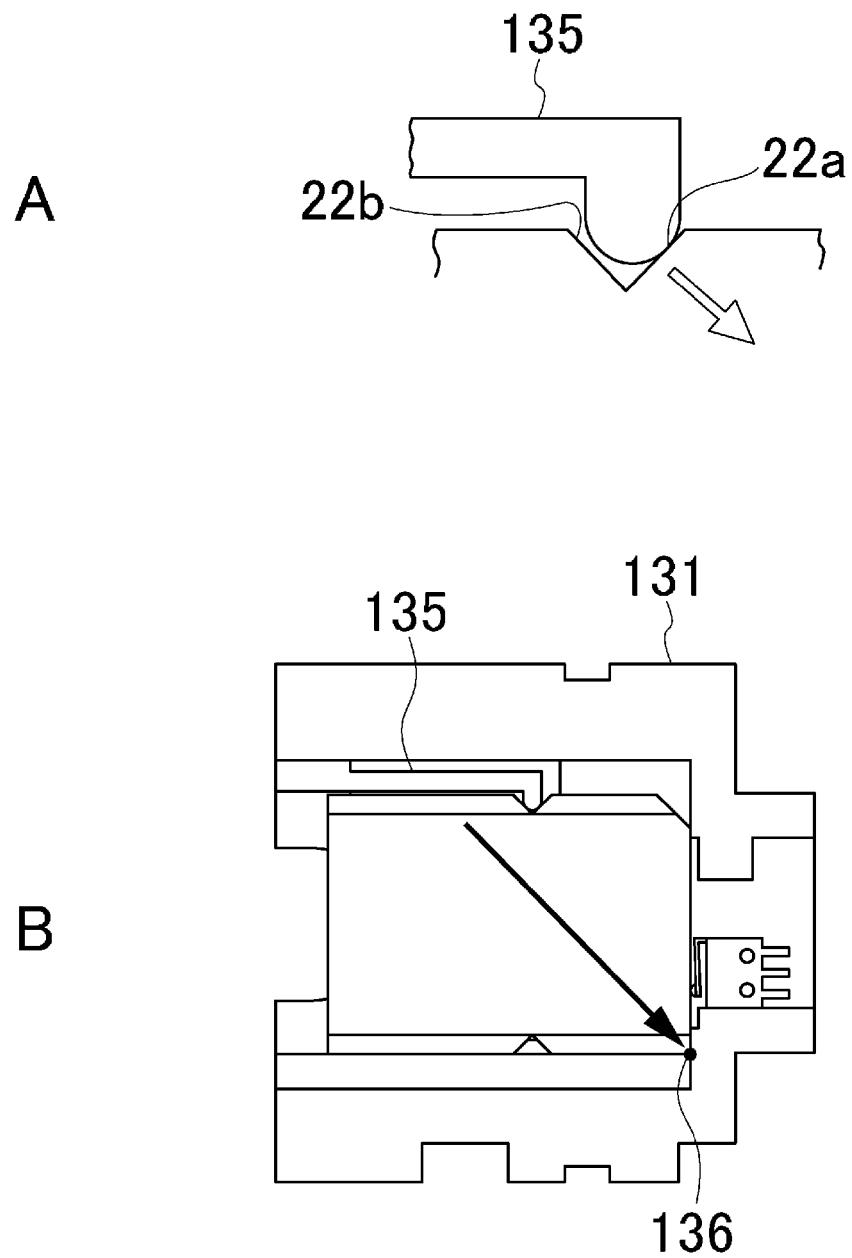
FIG. 10 is a diagram illustrating a positioning function of the lever 135.

FIG. 8 and FIG. 9 illustrate a configuration of the holder outer frame 131. In these diagrams, illustration of the holder inner frame 132 is omitted. A lever 135 having a hook-shaped tip portion is provided on the holder outer frame 131 extending in the insertion direction of the microchip 2. When the microchip 2 is inserted, the tip portion of the lever 135 contacts a notch 23 formed by obliquely cutting one of the four corners of the microchip 2 (refer to FIG. 9A). The lever 135 is flexible, and thus accommodates further insertion of the microchip 2 by flexing due to the force applied on the tip portion by the contact with the notch 23. Although the shape of the tip portion of the lever 135 is not especially limited, it is preferred that the shape is a curve like that illustrated in the diagrams.

Even when the microchip 2 is inserted in a mistaken insertion direction, as illustrated in FIG. 9B, the corners of the microchip 2 where the notch 23 is not formed engage with the curved portion of the tip portion formed in the shape of a hook of the lever 135. Consequently, the lever 135 prevents further insertion of the microchip 2 without flexing. As a result, mistaken insertion of the microchip 2 is prevented. To make the above-described engagement occur more easily, it is preferred that the curve angle of the curved portion of the lever 135 is set to 90° with respect to the corner of the microchip 2.

When the microchip 2 is inserted in the correct direction, the tip portion of the lever 135 that has been flexed by the contact with the notch 23 slides across a face on which a V groove 22 of the inserted microchip 2 is formed, and then fits into the V groove 22 (refer to FIG. 8B). The tip portion of the lever 135 and the V groove 22 are arranged in a positional relationship in which when the microchip 2 has been inserted as far as a position where the microchip 2 hits the chip detection sensor 133, the tip portion of the lever 135 fits into the V groove 22. It is noted that, although an example has been described here in which the V groove 22 is provided on each of two opposing faces of the microchip 2, it is sufficient if the V groove 22 is provided on the one face that the tip portion of the lever 135 slides across during insertion into the chip holder 13.

Of the two faces forming the V groove 22, the tip portion of the lever 135 that fits into the V groove 22 is in contact with only the face positioned on the far side in the insertion direction. The face of the V groove 22 that is in contact with the tip portion of the lever 135 is indicated by the reference sign 22a in FIG. 10, and the non-contact face is indicated by reference sign 22b. Due to the flexibility of the lever 135, the lever 135 applies a force on the contact face 22a pressing in the direction indicated by the arrow in the diagram. The microchip 2 is pressed by this force toward the reference point indicated by reference sign 136 in the diagram, and is positioned in the chip holder 13.

(4) Microchip

The microchip 2 to be mounted in the nucleic acid analysis apparatus 1a is not especially limited, as long as a region (wells) serving as the reaction site of the nucleic acid amplification reaction is provided. It is preferred that in the microchip 2 the above-described V groove 22 is formed on a side peripheral portion. Further, it is preferred that the above-described notch 23 is formed on one of the four corners.

The microchip 2 can be formed by laminating a substrate layer in which the wells and the like are formed. The molding of the substrate layer can be carried out by, for example, wet etching or dry etching of a glass substrate layer, or by nano-imprinting, injection molding, or cutting of a plastic substrate layer. Further, the lamination of the substrate layer can be carried out by a known method, such as thermal fusion bonding, anodic bonding, bonding using an adhesive sheet, plasma activated bonding, and ultrasonic bonding.

The material of the substrate layer may be various plastics, such as polydimethylsiloxane (PDMS), PMMA (polymethyl methacrylate: acrylic resin), PC (polycarbonate), PS (polystyrene), PP (polypropylene), PE (polyethylene), and PET (polyethylene terephthalate), and glass. It is preferred to select as the substrate layer material a material that is transmissive to light and that has little optical error due to having little intrinsic fluorescence and a small wavelength dispersion.

2. Nucleic Acid Analysis Apparatus Operation

Figure 11:
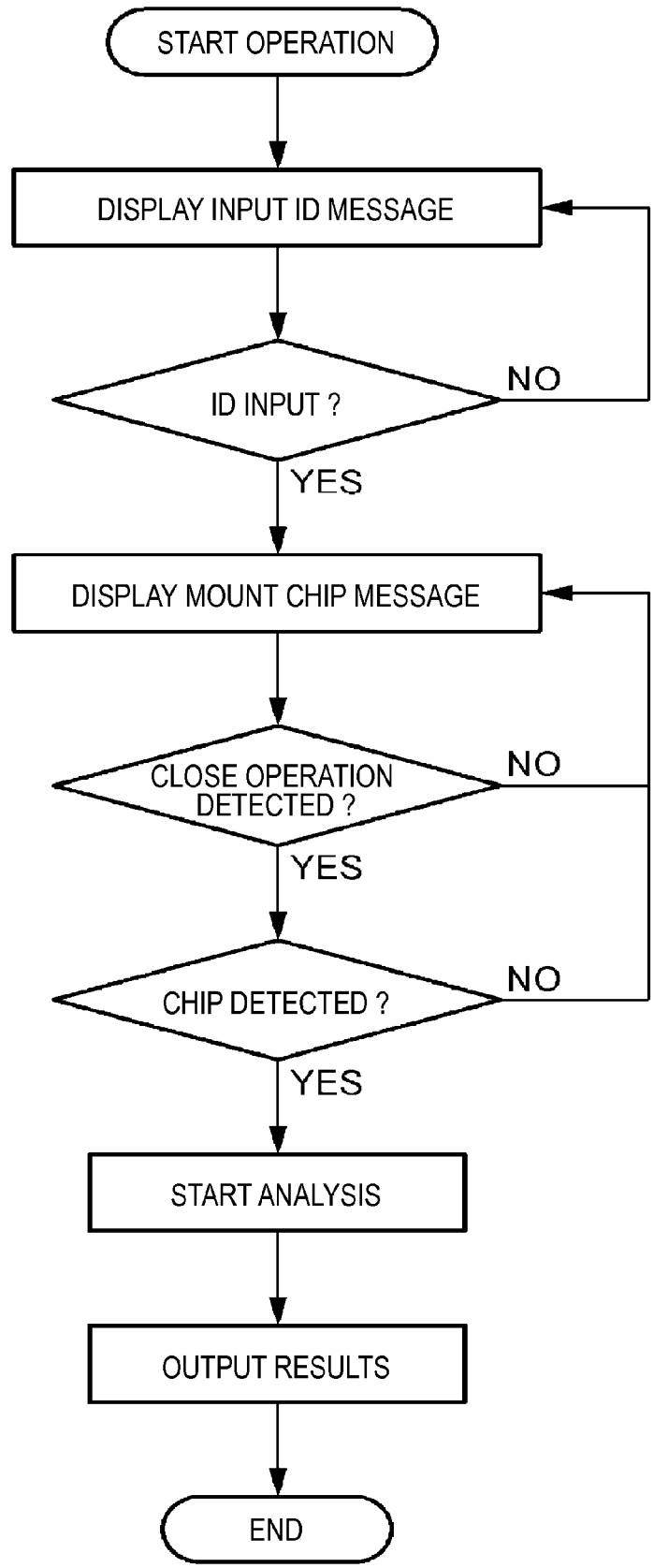

Next, operation of the nucleic acid analysis apparatus 1a will be described together with the procedure for mounting the microchip 2 in the nucleic acid analysis apparatus 1a. FIG. 11 illustrates an operation flowchart of the nucleic acid analysis apparatus 1a.

When starting analysis, first, operation of the apparatus is started by pressing a key (power button) provided on an upper face of the body of the nucleic acid analysis apparatus 1a.

When operation starts, the nucleic acid analysis apparatus 1a displays an input ID message on a compact display provided on the upper face of the body to prompt the user to input the chip ID and the analyte ID. Input of the chip ID and the analyte ID is performed with a code reader or a keyboard included on the input/output interface 1c. Further, after operation has started, the nucleic acid analysis apparatus 1a starts heating of the upper heater 111 of the upper unit 11 and the lower heater 121 of the lower unit 12 to preheat these heaters to the reaction temperature of the nucleic acid amplification reaction.

When ID input by the user has been confirmed, the nucleic acid analysis apparatus 1a displays a mount chip message on the compact display provided on the upper face of the body to prompt the user to mount the chip. Simultaneously with this, the nucleic acid analysis apparatus 1a releases the lock on the upper unit 11 and the lower unit 12 to enable the upper unit 11 to be opened. If ID input by the user is not confirmed, the nucleic acid analysis apparatus 1a maintains the lock on the upper unit 11 and the lower unit 12 to prevent a microchip 2 with the wrong ID from being mounted and analyzed.

When mounting the microchip 2 in the nucleic acid analysis apparatus 1a, first, the chip holder 13 is moved to the first holding position, in which the microchip 2 is held in midair, in coordination with the opening operation of the upper unit 11 and the lower unit 12. Specifically, the upper unit 11 is opened by pressing a key (eject button) provided on the upper face of the body of the nucleic acid analysis apparatus 1a (refer to FIGS. 3 and 5). When the upper unit 11 opens, the chip holder 13 flips up in coordination with this, and separates from the upper unit 11 and the lower unit 12 (first holding position).

Next, the microchip 2 is inserted from the insertion opening 134 of the chip holder 13 until it hits the chip detection sensor 133 (refer to FIG. 6B). The microchip 2 that has been inserted into the chip holder 13 is held in midair without contacting the upper heater 111 arranged in the upper unit 11 and the lower heater 121 arranged in the lower unit 12. Consequently, the microchip 2 can be prevented from being heated by the pre-heated upper heater 111 and lower heater 121.

Next, the chip holder 13 is moved to the second holding position by bringing the microchip 2 into contact with the upper heater 111 and the lower heater 121 in coordination with the closing operation of the upper unit 11 and the lower unit 12. Specifically, when the upper unit 11 and the lower unit 12 are closed so as to restrain the chip holder 13 with the upper unit 11, the chip holder 13 is sandwiched between the upper unit 11 and the lower unit 12 (refer to FIG. 2). Consequently, the chip holder 13 moves to a position in which the microchip 2 is held in contact with the upper heater 111 and the lower heater 121 (the second holding position), and heating of the microchip 2 is started.

The nucleic acid analysis apparatus 1a automatically starts analysis when the closing operation of the upper unit 11 and the lower unit 12 is detected by the opening/closing detection sensor 161, and the microchip 2 is detected by the chip detection sensor 133. Consequently, in the nucleic acid analysis apparatus 1a, immediately after the upper unit 11 and the lower unit 12 have closed, the heating and the analysis of the microchip 2 by the upper heater 111 and the lower heater 121 are simultaneously started. Therefore, in the nucleic acid analysis apparatus 1a, the start time of the nucleic acid amplification reaction and the start time of analysis can be precisely matched, which enables the reaction time to be strictly controlled and accurate analysis results to be obtained with a high reproducibility.

After analysis has started, the nucleic acid analysis apparatus 1a locks the upper unit 11 and the lower unit 12 so that the upper unit 11 is not opened by mistake during analysis. It is noted that even if ID input by the user has been confirmed, analysis is not started as long as the close operation of the upper unit 11 and the lower unit 12 has not been detected by the opening/closing detection sensor. Further, even if the close operation of the upper unit 11 and the lower unit 12 has been detected by the opening/closing detection sensor, analysis is not started as long as the microchip 2 is not detected by the chip detection sensor.

When analysis is complete, the nucleic acid analysis apparatus 1a outputs the analysis results to a printer, a display or the like included in the input/output interface 1c. After analysis has finished, the eject button is pressed to open the upper unit 11, the chip holder 13 again moves to the first holding position, and the microchip 2 is removed from the chip holder 13. After the microchip 2 has been removed from the chip holder 13, the upper unit 11 and the lower unit 12 are closed. At this stage, forgetting to remove the microchip 2 can be prevented by configuring so that the upper unit 11 and the lower unit 12 are not locked while the microchip 2 still remains pressed into the chip holder 13.

3. Analysis Apparatus

In the nucleic acid analysis apparatus 1a, after the microchip 2 has been mounted in the chip holder 13, the microchip 2 is brought into contact with the upper heater 111 and the lower heater 121 by closing the upper unit 11, and analysis is simultaneously started. Therefore, in the nucleic acid analysis apparatus 1a, in the nucleic acid analysis apparatus 1a, the time at which the nucleic acid amplification reaction starts by heating the wells 21 to the reaction temperature and the start time of analysis can be precisely matched, which enables accurate analysis results to be obtained with a high reproducibility.

The configuration of such a nucleic acid analysis apparatus 1a can also be applied to a microchip type analysis apparatus that is used for analyzing reactions other than a nucleic acid amplification reaction. Namely, the same configuration can be widely applied in apparatuses that perform analysis by making a material reaction equivalent to a nucleic acid amplification reaction progress by physical or chemical induction equivalent to heating. By employing the same configuration, in various types of microchip type analysis apparatus, analysis can be started simultaneously with the reaction being started in the wells by bringing the microchip mounted in the chip holder into contact with a reaction induction unit.

Additionally, the nucleic acid analysis apparatus according to the present technology may also be configured as below.

(1)

A nucleic acid analysis apparatus, including:

a heating unit configured to apply heat by contacting a microchip; and a chip holding unit configured to change a position between a first holding position that holds the microchip in midair and a second holding position that holds the microchip in contact with the heating unit.

(2)

The nucleic acid analysis apparatus according to (1), further including:

an opening/closing structure configured from a hinge, wherein the chip holding unit is connected by the hinge and moves between the first holding position and the second holding position in coordination with opening and closing of the opening/closing structure.

(3)

The nucleic acid analysis apparatus according to (2), wherein the chip holding unit moves to the first holding position in coordination with an opening operation of the opening/closing structure, and moves to the second holding position in coordination with a closing operation of the opening/closing structure.

(4)

The nucleic acid analysis apparatus according to any one of (1) to (3), wherein an insertion opening of the microchip is included in the chip holding unit, and wherein a shape of the insertion opening is a perpendicular cross-section shape of the microchip in an insertion direction.

(5)

The nucleic acid analysis apparatus according to (4), wherein the chip holding unit includes a flexible member having a hook-shaped tip portion extending in the insertion direction of the microchip, and wherein, in a state in which the microchip is inserted in the chip holding unit, the tip portion of the flexible member fits into a groove formed on a side peripheral portion of the microchip.

(6)

The nucleic acid analysis apparatus according to (5), wherein, in a state in which the microchip is inserted in the chip holding unit, the tip portion of the flexible member abuts only one face of the groove formed in a V shape, and urges the microchip in the insertion direction.

(7)

The nucleic acid analysis apparatus according to any one of (2) to (6), further including:

an upper unit and a lower unit that are each connected by the hinge in a manner that enables them to be opened and closed, and each include the heating unit.

(8)

The nucleic acid analysis apparatus according to (7), wherein a sensor configured to detect opening and closing and a protrusion that contacts the sensor are provided on the upper unit and the lower unit.

(9)

The nucleic acid analysis apparatus according to any one of (4) to (8), wherein a sensor configured to detect the inserted microchip is provided in the chip holding unit.

(10)

The nucleic acid analysis apparatus according to any one of (7) to (9), wherein the lower unit includes a light source, a lens, an optical filter, and a lower heater, and wherein the upper unit includes an upper heater, a detection filter, a lens, and a detector.

(11)

The nucleic acid analysis apparatus according to (10), wherein the light source is an LED array, and the detector is a PDIC array.

(12)

The nucleic acid analysis apparatus according to (1) to (11), further including:

a reading device of an identifier attached to the microchip.

Additionally, the microchip for nucleic acid analysis according to the present technology may also be configured as below.

(13)

A microchip for nucleic acid analysis that has a square shape, and has a V-shaped groove formed on a side peripheral portion for positioning a mounting position in the nucleic acid analysis apparatus.

(14)

The microchip for nucleic acid analysis according to (13), wherein a notch for defining an insertion direction into an insertion opening provided in the nucleic acid analysis apparatus is formed on one of four corners.

(15)

The microchip for nucleic acid analysis according to (13) or (14), formed from a plurality of substrate layers of different sizes.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

1*a* nucleic acid analysis apparatus
1*b* AC adapter
1*c* input/output interface
11 upper unit
111 upper heater
12 lower unit
121 lower heater
13 chip holder
131 holder outer frame
132 holder inner frame
133 chip detection sensor
134 insertion opening
135 lever
136 reference point
14 hinge
15 braking member
161 opening/closing detection sensor
162 protrusion
2 microchip
21 reaction area (wells)
22 V groove
22*a* contact face
22*b* non-contact face
23 notch

The invention claimed is:

1. A nucleic acid analysis apparatus, comprising:
a heater configured to apply heat to a microchip based on a contact between the heater and the microchip; and
a chip holder configured to change a position of the microchip between a first holding position and a second holding position, wherein the chip holder comprises:
an insertion opening configured to receive the microchip based on insertion of the microchip into the chip holder; and
a flexible member having a hook-shaped tip portion that extends along a direction of the insertion of the microchip,
wherein at the first holding position, the chip holder is further configured to hold the microchip in midair, and
wherein at the second holding position, the chip holder is further configured to hold the microchip in contact with the heater.

2. The nucleic acid analysis apparatus according to claim 1, further comprising:
an opening/closing structure connected to a hinge,
wherein the chip holder is connected to the hinge, and
wherein the chip holder is further configured to move between the first holding position and the second holding position based on an opening operation and a closing operation of the opening/closing structure.

3. The nucleic acid analysis apparatus according to claim 2, wherein the chip holder is further configured to:
move to the first holding position based on the opening operation of the opening/closing structure; and
move to the second holding position based on the closing operation of the opening/closing structure.

4. The nucleic acid analysis apparatus according to claim 1,
wherein a shape of the insertion opening is a perpendicular cross-section shape of the microchip in the direction of the insertion.

5. The nucleic acid analysis apparatus according to claim 1, wherein the hook-shaped tip portion of the flexible member is configured to fit into a groove on a side peripheral portion of the microchip based on the insertion of the microchip into the chip holder.

6. The nucleic acid analysis apparatus according to claim 5, wherein the hook-shaped tip portion of the flexible member is further configured to:
abut one face of the groove with a V shape; and
urge the microchip in the direction of the insertion.

7. The nucleic acid analysis apparatus according to claim 2, further comprising:
an upper unit and a lower unit, each connected to the hinge,
wherein the hinge is configured to enable at least one of the upper unit or the lower unit to one of open or close.

8. The nucleic acid analysis apparatus according to claim 7, further comprising a first sensor configured to detect at least one of an opening state or a closing state of at least one of the upper unit or the lower unit.

9. The nucleic acid analysis apparatus according to claim 5, wherein the chip holder further comprises a second sensor configured to detect the microchip that is inserted.

10. The nucleic acid analysis apparatus according to claim 7,
wherein the lower unit includes a light source, a first lens, an optical filter, and a lower heater, and
wherein the upper unit includes an upper heater, a detection filter, a second lens, and a detector.

11. The nucleic acid analysis apparatus according to claim 10,
wherein the light source is an LED array, and
wherein the detector is a PDIC array.

12. The nucleic acid analysis apparatus according to claim 1, further comprising a reading device of an identifier attached to the microchip.

13. A system, comprising:
a nucleic acid analysis apparatus; and
a microchip including a V-shaped groove on a side peripheral portion of the microchip and configured to mount the microchip in a mounting position in the nucleic acid analysis apparatus;
wherein the nucleic acid analysis apparatus comprises:

a heater configured to apply heat to the microchip based on a contact with the microchip; and a chip holder configured to change a position of the microchip between a first holding position and a second holding position, wherein the chip holder comprises:

an insertion opening configured to receive the microchip based on insertion of the microchip into the chip holder; and a flexible member having a hook-shaped tip portion that extends along a direction of the insertion of the microchip, wherein at the first holding position, the chip holder is further configured to hold the microchip in midair, and wherein at the second holding position, the chip holder is further configured to hold the microchip in contact with the heater.

14. The microchip for nucleic acid analysis according to claim 13, further comprising a notch on one of four corners of the microchip, wherein the notch is configured to define the direction of the insertion into the insertion opening in the nucleic acid analysis apparatus.

15. The microchip for nucleic acid analysis according to claim 13, further comprising a plurality of substrate layers of different sizes.

16. A method for mounting a microchip in a nucleic acid analysis apparatus, the method comprising:

moving a chip holder to a first holding position, based on an opening operation of an opening/closing structure of the nucleic acid analysis apparatus, wherein a first edge of the chip holder is connected to the opening/closing structure via a hinge, wherein the chip holder comprises:

an insertion opening configured to receive the microchip based on insertion of the microchip into the chip holder; and a flexible member having a hook-shaped tip portion that extends along a direction of the insertion of the microchip, and wherein at the first holding position, a distal edge of the chip holder opposite to the first edge, is in midair;

mounting the microchip in the chip holder; and moving the chip holder with the mounted microchip to a second holding position, based on a closing operation of the opening/closing structure, wherein at the second holding position, the chip holder is configured to hold the microchip in contact with the opening/closing structure.

17. An analysis apparatus, comprising:

a heater configured to apply heat to a microchip based on a contact between the heater and the microchip;

a light source configured to emit light on the microchip; and a chip holder configured to change a position of the microchip between a first holding position and a second holding position, wherein the chip holder comprises:

an insertion opening configured to receive the microchip based on insertion of the microchip into the chip holder; and a flexible member having a hook-shaped tip portion that extends along a direction of the insertion of the microchip, wherein at the first holding position, the chip holder is further configured to hold the microchip in midair, and wherein at the second holding position, the chip holder is further configured to hold the microchip in contact with the heater.

18. A nucleic acid analysis apparatus, comprising:

a heater configured to apply heat to a microchip based on a contact between the heater and the microchip; and a chip holder configured to change a position of the microchip between a first holding position and a second holding position, wherein the chip holder comprises:

an insertion opening configured to receive the microchip based on insertion of the microchip into the chip holder; and a flexible member having a hook-shaped tip portion that extends along a direction of the insertion of the microchip, wherein the hook-shaped tip portion is configured to fit into a groove on a side peripheral portion of the microchip, based on the insertion of the microchip in the chip holder, wherein at the first holding position, the chip holder is further configured to hold the microchip in midair, and wherein at the second holding position, the chip holder is further configured to hold the microchip in contact with the heater.

\* \* \* \* \*